United States Patent [19]

Loo et al.

[11] Patent Number: 5,041,087

[45] Date of Patent: Aug. 20, 1991

[54] NEEDLE-LESS PARENTERAL FLUID INJECTOR

[76] Inventors: George D. H. Loo, 9814 Curwood Pl., Beverly Hills, Calif. 90210; Gordon A. Wong, 118 Northlite Cir., Sacramento, Calif. 95831

[21] Appl. No.: 531,864

[22] Filed: May 31, 1990

Related U.S. Application Data

[63] Continuation of Ser. No. 231,090, Aug. 11, 1988, abandoned.

[51] Int. Cl.$^5$ .............................................. A61M 5/00
[52] U.S. Cl. .................................... 604/83; 604/247; 137/533; 251/149.6
[58] Field of Search ...................... 604/33, 80, 81, 82, 604/83, 84, 122, 123, 124, 125, 247, 249; 251/149.6, 149.7; 137/533, 614.2

[56] References Cited

U.S. PATENT DOCUMENTS

| | | | |
|---|---|---|---|
| 3,806,086 | 4/1974 | Cloyd | 251/149.7 |
| 4,005,710 | 2/1977 | Zeddies et al. | 137/533 |
| 4,103,686 | 8/1978 | LeFevre | 137/614.21 |
| 4,310,017 | 1/1982 | Raines | 137/533 |
| 4,324,239 | 4/1982 | Gordon et al. | 604/122 |
| 4,638,668 | 1/1987 | Leverberg et al. | 251/149.7 |
| 4,722,725 | 2/1988 | Sawyer et al. | 604/27 |
| 4,758,224 | 7/1988 | Siposs | 604/247 |
| 4,871,353 | 10/1989 | Thomsen | 604/83 |

FOREIGN PATENT DOCUMENTS

| | | | |
|---|---|---|---|
| 0737249 | 6/1966 | Canada | 604/247 |
| 3520044 | 12/1986 | Fed. Rep. of Germany | 604/83 |

Primary Examiner—C. Fred Rosenbaum
Assistant Examiner—William W. Lewis
Attorney, Agent, or Firm—Limbach, Limbach & Sutton

[57] ABSTRACT

A fluid injector for use with a needle-less syringe or needle-less add-on IV line is disclosed. The injector is connected to a main IV line and has a fluid passageway from the syringe or the add-on IV set to the main IV line. The injector comprises an anti-backflow valve member where the member is movable under fluid pressure alone between a first position where the fluid can flow through the injector and a second position where the fluid cannot flow through the injector. The injector also comprises a valve located near the syringe end of the injector for receiving the fluid from the syringe or the add-on IV line for injection into the main IV line and for preventing air embolus entering into the IV line. The injector permits leaving a single or a group of drug filled syringes on line at all times with a continuously, rapidly flowing IV line and provides instantaneous "on demand" delivery of drugs or fluids from the syringe. The injector also prevents backflow of IV fluid into the syringe and automatically prevents air embolus from entering into the IV line whenever a syringe is removed from it for refilling it or replacing it with one containing another medication. The injector also permits addition of fluids to a continually flowing main IV stream manually, by pushing the plunger of the syringe by hand, mechanically, by using a programmed electronic infusion pump, or simply, by gravity drip from an add-on "piggy-back" IV set.

11 Claims, 7 Drawing Sheets

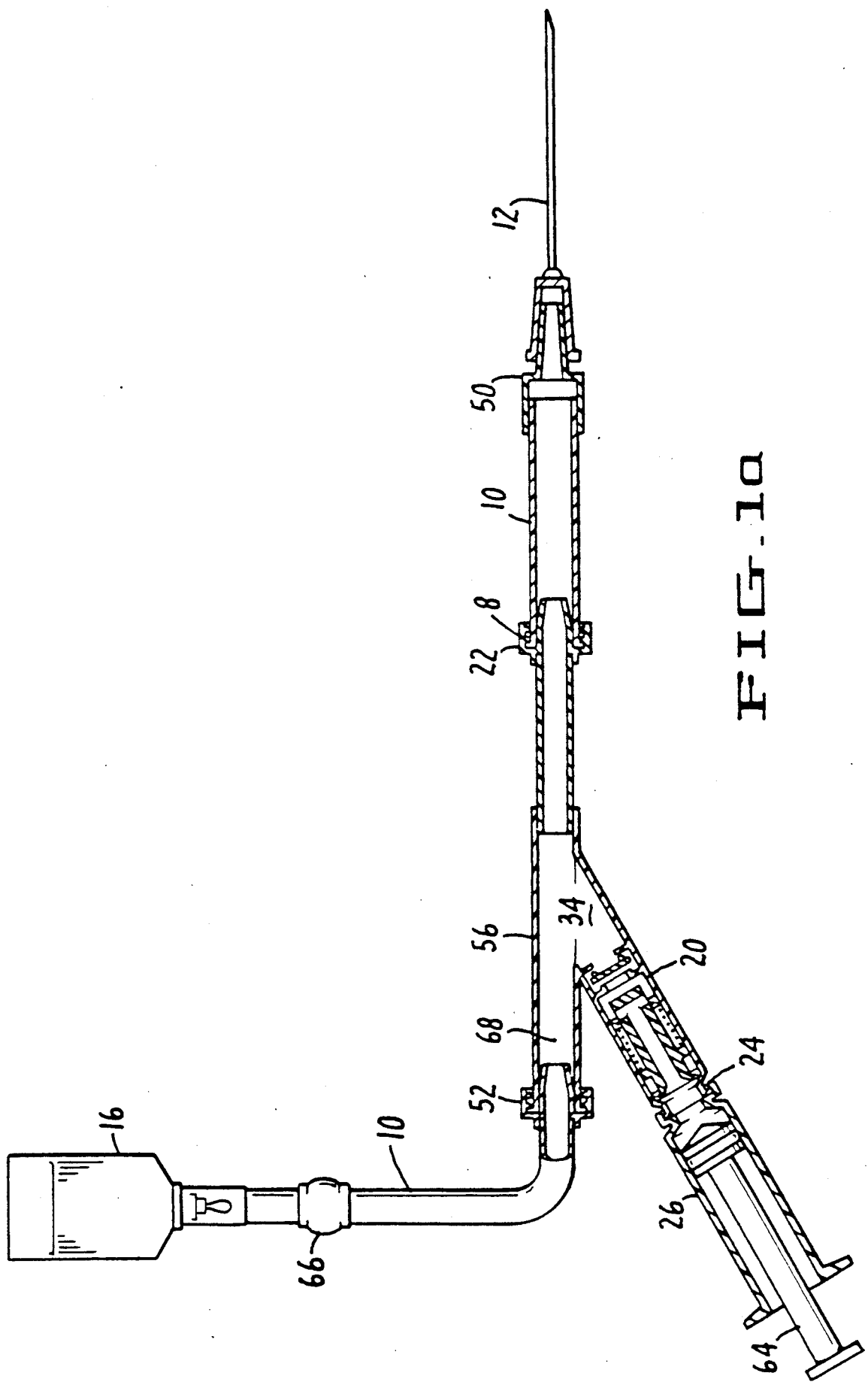

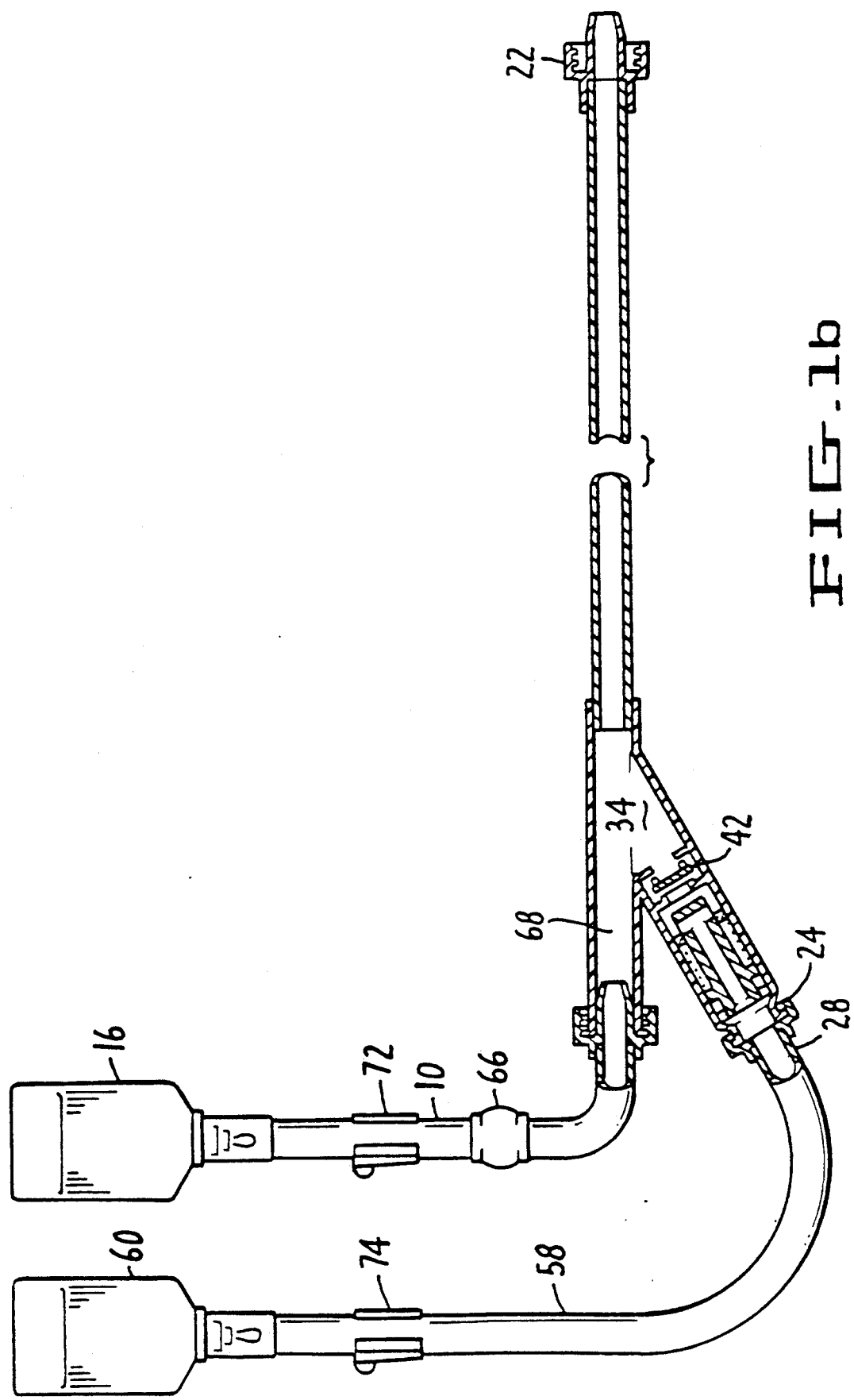

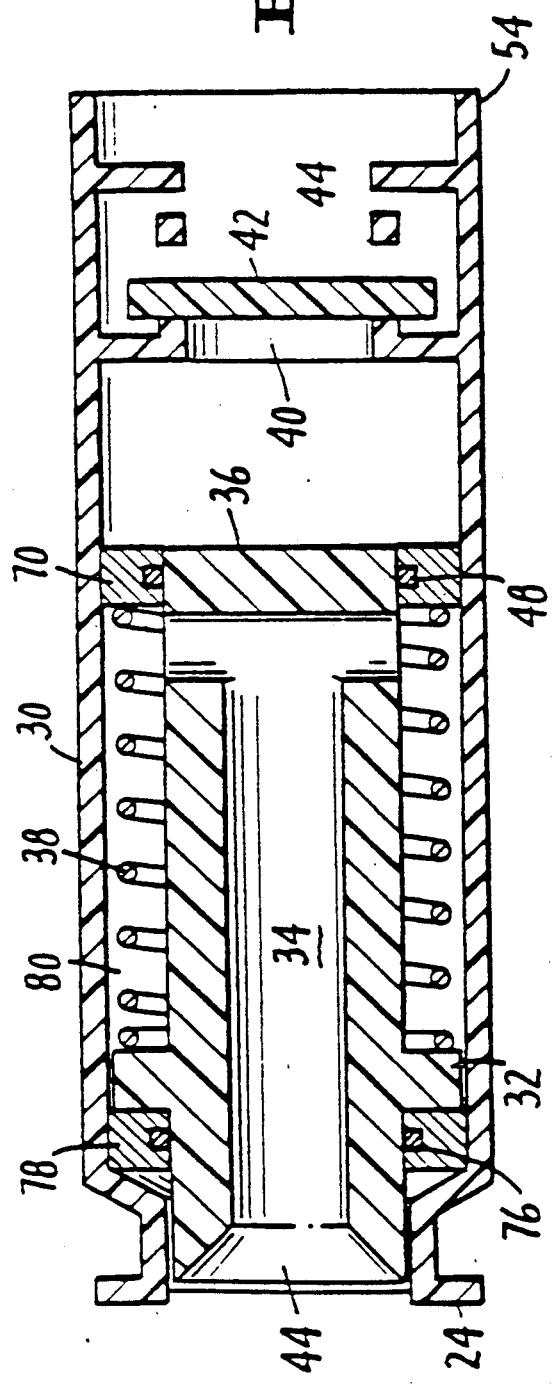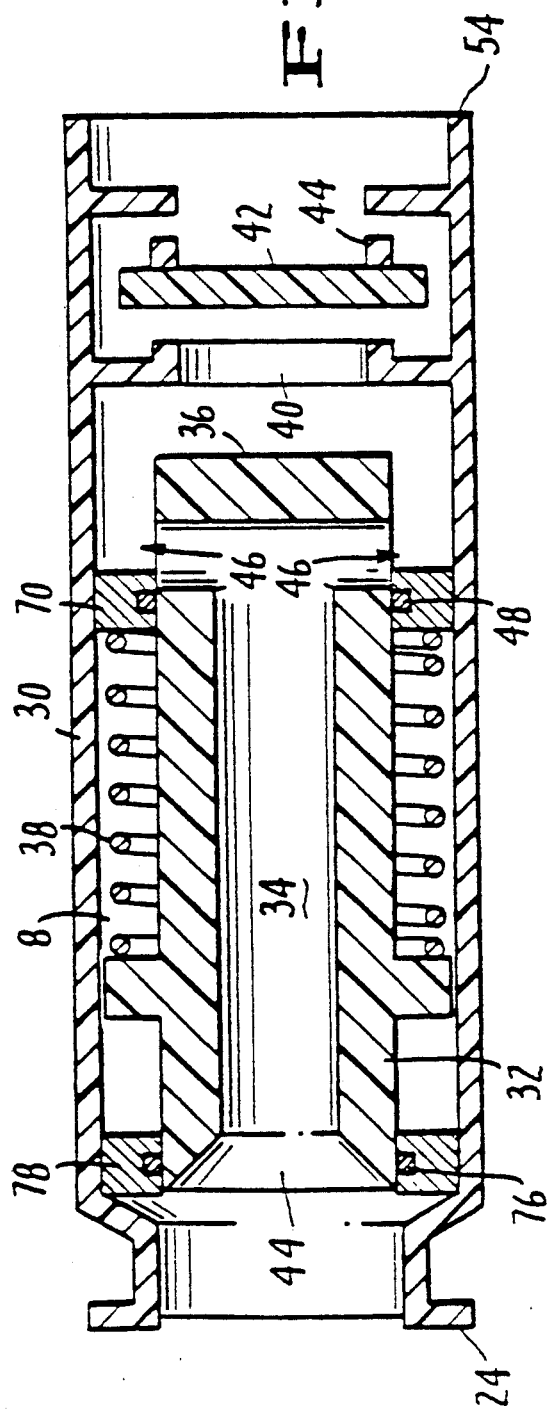

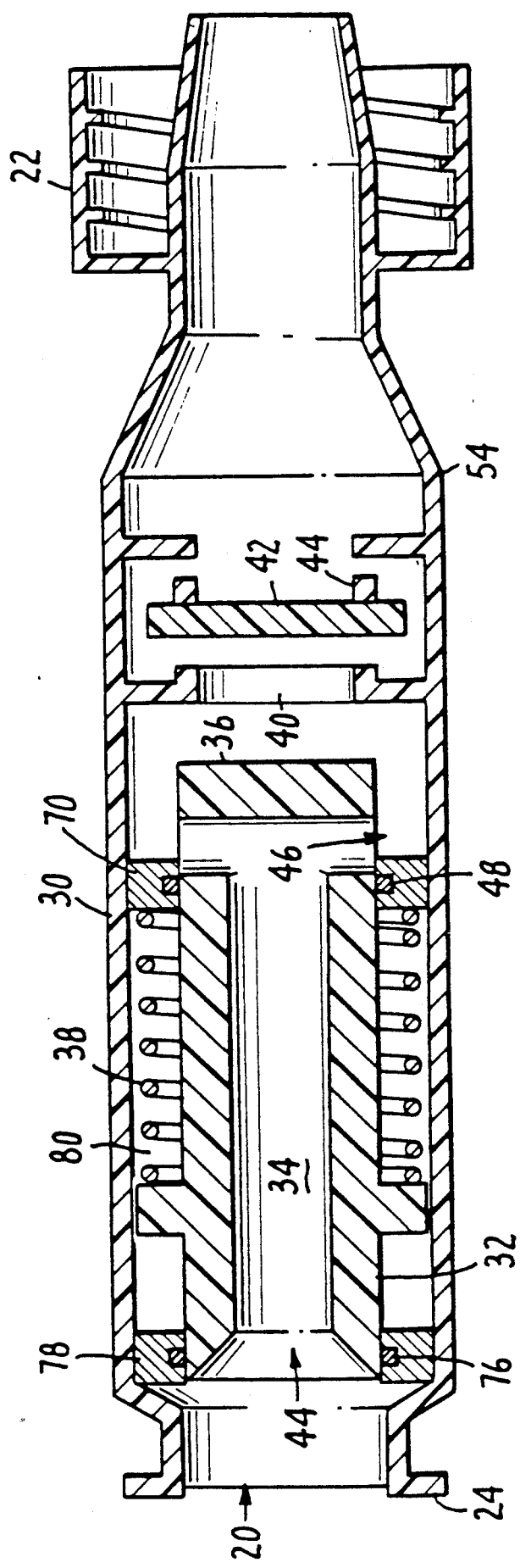

NEEDLE-LESS PARENTERAL FLUID INJECTOR

This is a continuation of application Ser. No. 07/231,090, filed Aug. 11, 1988, now abandoned.

TECHNICAL BACKGROUND

The present invention relates to an improved needle-less parenteral fluid injector which is more efficient and is safer for both the health-care worker as well as the patient.

BACKGROUND OF THE INVENTION

In the health care profession, intravenous injection of fluids and drugs are routinely administered. A typical application is in the surgical field where anesthetics, such as barbiturates, sedatives, and narcotics are usually administered to a patient who has an intravenous (IV) line attached. Thus, in a typical surgical procedure, at various times, or at any one time, a number of different drugs or fluids must be administered to the patient.

Typically in anesthesia, medications are given on a "when needed basis". This varies with different patients, depending upon factors such as age, weight, sex, medical disease and individual metabolism. When medications are needed, they are usually administered on the basis of "the sooner the better". In the prior art, the method of administering medications to a patient through an IV line is performed in the following five steps (assuming that the fluid or medication is already in a needled syringe): (1) uncap the needle on the syringe; (2) rapidly, but carefully, insert the needle into a rubber plug port in the IV line; (3) inject the medication; (4) withdraw the needle from the rubber plug port; (5) carefully recap the needle to preserve sterility and to protect the health care worker from a source of accidental skin puncture from a possible blood-borne-disease contaminated needle. Needle sticks have been the most frequently reported injury to health care workers in American hospitals. Recently the Center For Disease Control in Atlanta, Ga., has recommended that anesthesiologists and nurses avoid recapping of needles after using them for injection into an IV line. This is to avoid exposing themselves to a risk of contracting contagious blood-borne diseases, such as AIDS, Hepatitis, etc., through accidental needle puncture when the needle on the syringe is recapped.

Guaiac testing, for occult blood, has shown the presence of blood in IV lines even though no blood was grossly visible, and the IV flow was considered to be anterograde at all times. Thus, IV fluid connected to any patient may contain infectious blood even though no blood is grossly visible. The possibility of accidental needle puncture with a potentially contaminated needle occurs twice during each normal intravenous injection. The first occurs when the needle is being inserted into the rubber plug port in the IV line. The second time, is when the needle is recapped after use.

During the course of an anesthetic treatment, many repeated, intermittent intravenous injections of medications and fluids are necessary. Thus, the number of times of potential exposure to a possibly contaminated needle puncture is manifold. In response to the Center For Disease Control findings and recommendations, many institutions, such as the University of California Hospitals in San Francisco, are recommending to their health care workers that needles should not be routinely recapped after use for intravenous injections. While this removes one problem associated with the present method, many other problems, such as efficiency of administering of the medication, still remain.

In the prior art, a number of needle-less fluid injection apparatuses are disclosed. For example, see U.S. Pat. Nos.: 3,994,293; 2,886,457; 3,416,567; 4,506,691; 4,585,435; 4,737,145; and 4,015,336. However, none of the references teaches or suggests an apparatus which is safe for the patient in that the apparatus provides for an anti-backflow valve and an anti-air embolus valve and permits simultaneous administration of multiple pressure infused medications and gravity drip IV fluid infusions.

SUMMARY OF THE INVENTION

In the present invention, a parenteral fluid and medication injector is disclosed. The injector has a fluid transport means with one end for connecting to a patient and a fluid input port for receiving a fluid. The injector comprises a fluid conduit having two ends. A first end of the fluid conduit has means to connect to the fluid input port of the fluid transport means. An anti-backflow valve member is in the fluid conduit. The anti-backflow valve member is movable under fluid pressure alone between a first position and a second position. In the first position, fluid can flow in the conduit between the two ends. In the second position, fluid cannot flow between the two ends of the conduit. Finally, a valve means is provided located at the second end of the fluid conduit for preventing air embolus in the fluid conduit and for receiving the fluid for injection into the fluid transport means.

BRIEF DESCRIPTION OF THE DRAWINGS

FIG. 1a is a schematic partial cross-sectional view of the parenteral fluid injector shown in FIG. 1 when used with a syringe device.

FIG. 1b is a schematic partial cross-sectional view of the parenteral fluid injector shown in FIG. 1 when used with a secondary or add-on IV set.

FIG. 2 is a cross-sectional view of the injector of the present invention shown in FIG. 1.

FIG. 5 is another embodiment of the parenteral fluid injector of the present invention for use in direct connection to a needle or IV catheter.

DETAILED DESCRIPTION OF THE DRAWINGS

Figure 1:
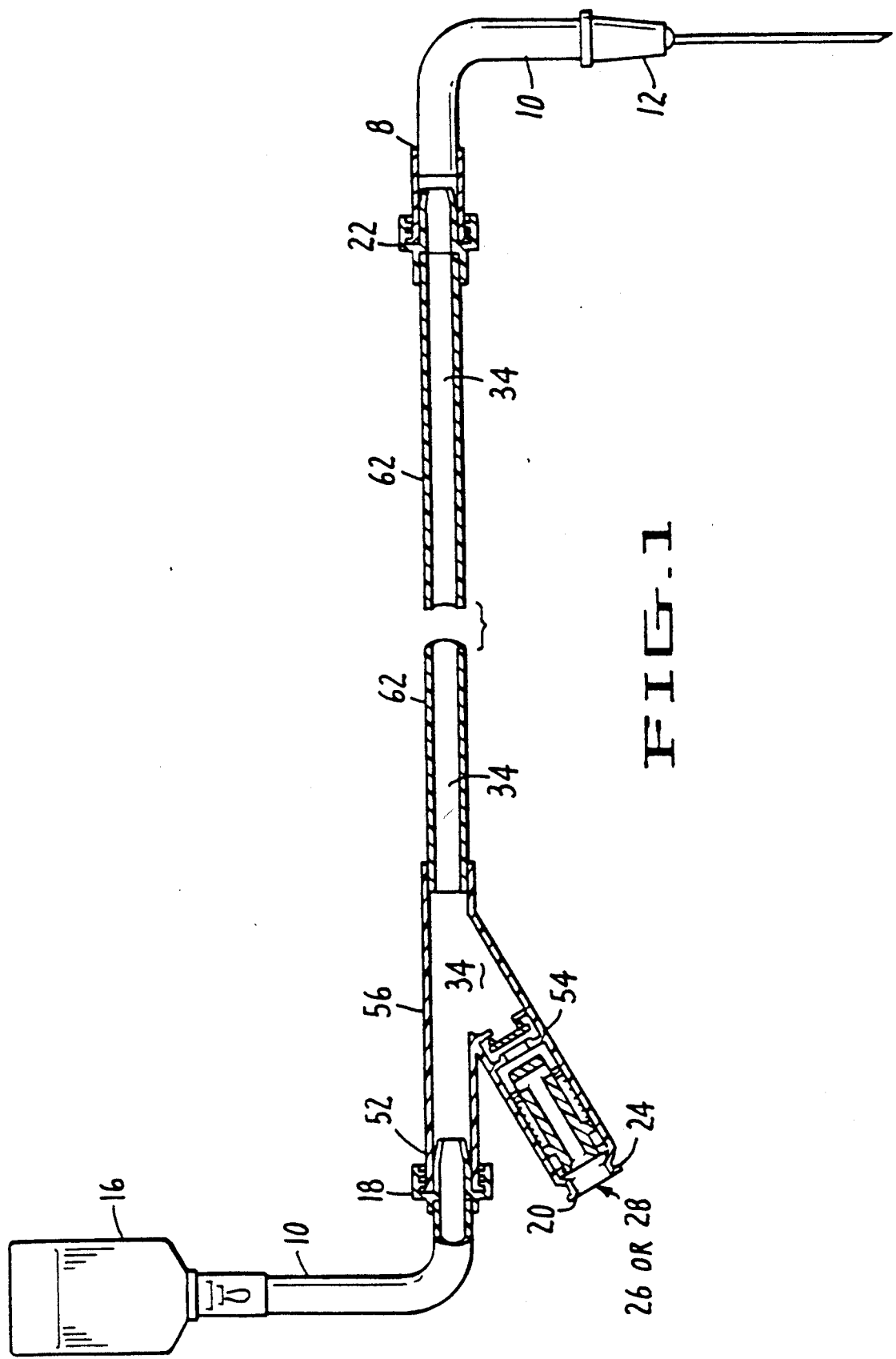
FIG. 1 is a schematic partial cross-sectional view of one embodiment of the parenteral fluid injector of the present invention for use with an intravenous (IV) line.

Referring to FIG. 1 there is shown a parenteral fluid injector 20 of the present invention for use interposed in an IV line 10. The IV line 10 has one end having a needle 12 attached thereto for connection to a patient. The IV line 10 also has another end 8 which is a fluid input port for receiving a fluid from the injector 20. The IV line 10 has another end 18 which is a fluid output port for inputting fluid from IV bottle 16 into a female luer lock connector 52 of injector 20. The injector 20 has one end 22 which is connected to the fluid input port 8 of the IV line 10. Male luer lock end 22 is connected to chamber 56 by a variable length of flexible tubing 62. The parenteral fluid injector 20 has another end 24 which is adapted to receive a needle-less syringe 26 or a needle-less add-on IV line tip connector 28 which delivers fluid into the injector 20, then into the IV flow stream 34 and then injector 20, then into the IV flow stream 34 and then into the IV line 10. Injector body 30 of the parenteral fluid injector 20 of the present invention has an outflow end 54 connecting injector valve body 30 to IV stream 34. Y-shaped chamber 56 of the injector 20 connects fluid channels from connector 22, connector 52 and connector 24 of the parenteral fluid injector 20.

Referring to FIG. 1a there is shown a schematic partial cross-sectional view of parenteral fluid injector 20 of the present invention when attached to a needle-less syringe 26 of any capacity. The plunger 64 of the syringe 26 may be pushed manually by hand or by a programmed electronic infusion pump to inject a precise medication dose at any instant. Fluid flow is from syringe 26, through injector 20, through fluid Y-shaped chamber 56, through male luer lock connector 22, through connector 8, and into IV tubing 10 going to needle in patient. Normally, when used in surgery, IV tubing 10 contains a built in check valve 66 to prevent backflow of syringe 26 contents from flowing towards IV bottle 16 during rapid injection of medication. When used with an IV tubing set not containing a check valve 66, tubing 10 would be pinched off manually between connector 52 and IV bottle 16. In another embodiment of the parenteral fluid injector of the present invention, another anti-backflow valve similar to the anti-backflow valve 42 of the injector 20, as shown in FIG. 2, would be built into injector 20 at position 68 as shown on FIG. 1a.

Referring to FIG. 1b there is shown a schematic partial cross-sectional view of parenteral fluid injector 20 of the present invention when attached to a needle-less tip 28 of an add-on (or piggy-back) IV tubing 58 connected to IV fluid container 60 on one end and to female luer lock connector 24 on the other end. In this configuration of use of the parenteral fluid injector of the present invention, both IV line 10 and IV line 58 can be run simultaneously. As will be explained, there will be no backflow into either IV tube 58 or IV tube 10 because of the valve 42 and valve 66. Gravity drip of IV fluid is possible simultaneously from IV bottle 16 and IV bottle 60.

Referring to FIG. 2 there is shown in greater detail one embodiment for the parenteral fluid injector 20 of the present invention. The injector 20 comprises a barrel shaped member 30 with a central fluid passage 34 therebetween. Near one end 54 of the injector 20 is an anti-backflow valve member 42. The anti-backflow valve member 42 in this embodiment is a disc-shaped member. Any other type of anti-backflow valve may also be used. The valve member 42 is movable between a first position and a second position. In the first position, the valve member 42 covers the aperture 40 which is in the fluid passageway 34 and prevents the flow of fluid from the one end 54 to the other end 24. In the second position, the valve member 42 comes to rest against a stop 44. Stop 44 may be built on as a part of the injector chamber 30 or it may be built on as part of disc member 42. However, the fluid flow in passageway 34 from the other end 24 to the one end 54 is maintained as the fluid flows around the disc 42 and to the one end 54. The valve member 42 is movable between the first position and the second position only by the difference in the pressure of the fluid from one side of the valve member 42 to the other side of the valve member 42. Thus, any pressure differential on the two sides of the valve member 42 causes the valve member 42 to move from the one position to the second position.

The injector 20 further comprises a piston-shaped member 32. The piston-shaped member 32 has a central bore which contains the fluid passageway 34. The piston 32 has a capped end 36 and an injection inlet port 44. The fluid passageway 34 receives fluid from the syringe 6 in a direction parallel to the axis of the piston 32. Near the capped end 36, the passageway 34 flows in a radial fluid passage 46.

The piston 32 is movable between a first position and a second position. When the piston is in the first position, the capped end 36 is immediately adjacent to and abuts an O-ring 48 which in turn is immediately adjacent to and abuts a ring retainer collar 70 built onto the cylindrical outer member 30. Thus, when the piston 32 is in the first position, atmospheric air, or fluid from the syringe 26 is prevented from flowing from the other end 24 of the injector 20 to the one end 54. The piston 32 is maintained in the first position by the stainless steel spring 38, or any other type of spring device, which urges against the piston 32 to maintain it in the first position.

The piston 32 is moved into the second position when the needle-less tip of the syringe 26 or the needle-less tip of an IV line 28 (FIG. 1b) is pushed into the other end 24 of the injector 20 and is mated to the injection inlet port 44 of the piston 32 and is pushed into the second position. Thereafter, the syringe is locked with the female luer lock connector 4, thereby maintaining the piston 32 in the second position. In the second position, the piston 32 is urged against stainless steel spring 38. In addition, the capped end 36 is pushed away from the O-ring 48, exposing the radial passage 46. This then permits fluid or medication to flow from the injection inlet port 44 to the one end 54 of the injector 20, past the anti-backflow valve member 42, and into the IV fluid tubing 10, and thus into the patient.

The injector 20 of the present invention further comprises another sealing O-ring, or similar sealing device, 76 which in turn is immediately adjacent to and abuts another stationary ring retainer part 78 of the cylindrical outer member 30 of the injector 20. The two sealing rings 48 and 76 and the two stationary ring retainers 70 and 78 on the cylindrical outer member 30 of the injector 20 form a chamber 80 which isolates the stainless steel spring 38 from communication with fluid in IV tubing 10, and thus patient contact, at all times.

This is explained as follows: When piston rod 32 is int the first position, as when neither needle-less syringe tip 26 or needle-less add-on IV tip 28 is connected to the injector 20, the chamber 34 of the piston rod 32 (Shown in FIG. 2) is sealed off from the IV fluid path 10 (and is thus also sealed off from continuity with patient body fluids). This is accomplished by sealed end 36 of piston rod 32, O-ring 48, and O-ring retainer 70. When the piston rod 32 is in the second position, as when a needle-less syringe tip 26 or a needle-less add-on IV tip 28 is attached to injector 20, fluid or medication from syringe 26 (FIG. 1A) or add-on IV 28 (FIG. 1B) flows into rod opening 44 (FIG. 2), into fluid path 34, out radial fluid passge 46, past anti-backflow disk member 42, and communicates with IV fluid path 10 and patient 14. At this time, spring chamber 80 is sealed off from all fluid contact by O-rings 48 and 76 and ring retainers 70 and 78.

The theory of operation of the parenteral fluid injector 20 of the present invention is as follows. Initially the needle-less syringe 26 with fluid therein or a needle-less IV tubing tip 28 with the fluid therein is locked onto the injector 20 at the other end 24 thereof which contains the female luer lock connector 24. The one end 22 (FIGS. 1, 1a1b, 4, and 5) is connected to the fluid port 8 of the IV line 10. The piston 32 of injector 20 is thus pushed into the second position as shown in FIG. 2. The plunger of the syringe 26 is pushed to fill the injector 20 and its component fluid chamber 34 with fluid and expel all air. Or, if an add-on IV tubing 58 is connected to connector 24 of injector 20 (FIG. 1b) clamp 74 is opened to fill injector 20 and its component fluid chamber 34 with fluid and expel all air. Then the IV clamp 72 (FIG. 1b) is opened to fill the entire fluid passageway with fluid and rid the injector 20 and the IV line 10 of any air therein. When pressure is applied to the syringe 26 or fluid is dripped out of tubing 58, fluid flows from the passageway 34 and the radial passageway 46 pushing the anti-backflow valve 42 into the second position. (As shown in FIG. 2). With the injector 20 and the IV line 10 filled with fluid, the injector 20 of the present invention and the main IV connected to IV fluid bottle 16 is now ready to be connected to needle 12 or IV catheter 12 inserted into the patient.

In this position, the syringe 26 can be left in place. since no pressure is applied to the syringe 26 and since the needle 12 is typically connected to a vein of a patient where there is a source of fluid pressure (IV fluid column hydrostatic pressure), there is a pressure differential between the two sides of the anti-backflow valve member 42 Thus the anti-backflow valve member 42 would return to the first position closing off the aperture 40 and preventing any fluid from the IV line 10 to flow back into the injector 20 and also into the syringe 26. In this manner, the syringe 26 may be left virtually indefinitely connected to the injector 20 of the present invention, without any fear of back flow fluid from the IV line 10 entering into syringe 26 and diluting the medication contained therein. In this position, the syringe 26 may be left and applied "on demand". Further, when pressure is applied to the syringe 26, the fluid would flow through the passageway 34 and into IV line 10. When it is desired to change the syringe 26 to another syringe that contains different fluid or medication, the syringe 26 is simply removed from the female luer lock connector 24. When the syringe 26 is so removed, the piston 32 is automatically retracted into the first position whereby the capped end 36 abuts the O-ring 48 and seals the passageway 34. Sealing of the passageway 34 prevents air embolus from entering into the IV line 10 and thus into the patient As can be seen from the foregoing, there are many advantages to the injector 20 of the present invention. First and foremost is that no needles are used (except initially when the needle 12 or the IV catheter 12 is inserted into the patient for connection to the IV line 10). Secondly, the syringe 26 can be left virtually indefinitely connected to the IV line 10 without any fear of back flow of fluid from the IV line 10 into the syringe 26. Thus the syringe 26 can be maintained on line and drugs will be ready to be administered on an immediate "as-needed basis". Finally, and most importantly, the injector 20 of the present invention automatically prevents the introduction of air embolus into the IV line 10, and thus into the patient, when the syringe 26 is removed or exchanged.

Figure 3:
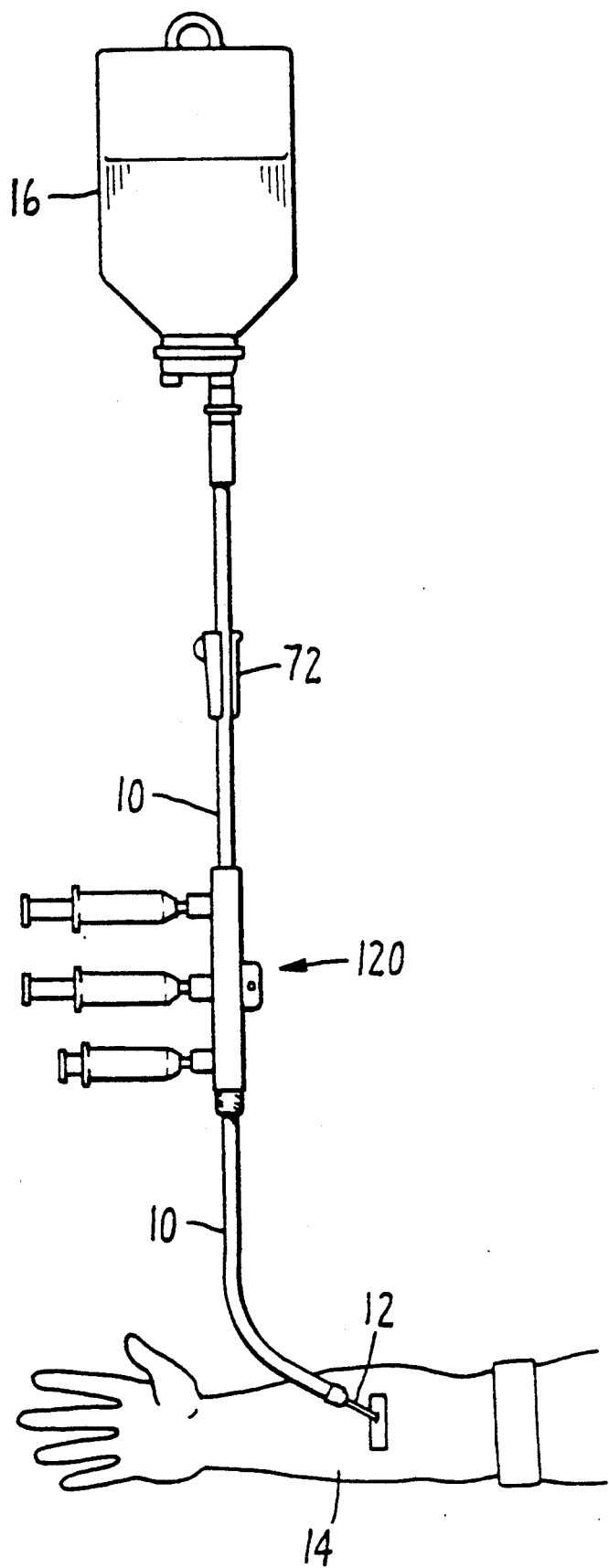
FIG. 3 is a schematic view of another embodiment of the parenteral fluid injector of the present invention for use with an IV line.

Referring to FIG. 3 there is shown another embodiment of an injector 120 of the present invention. The injector 120 is shown connected to an IV line 10 with a needle 12 or IV catheter 12 at one end connected to a patient 14. Another end of the IV line 10 is a source of fluid, such as glucose. The injector 120 is placed "in-line" with the IV line 10.

Figure 4:
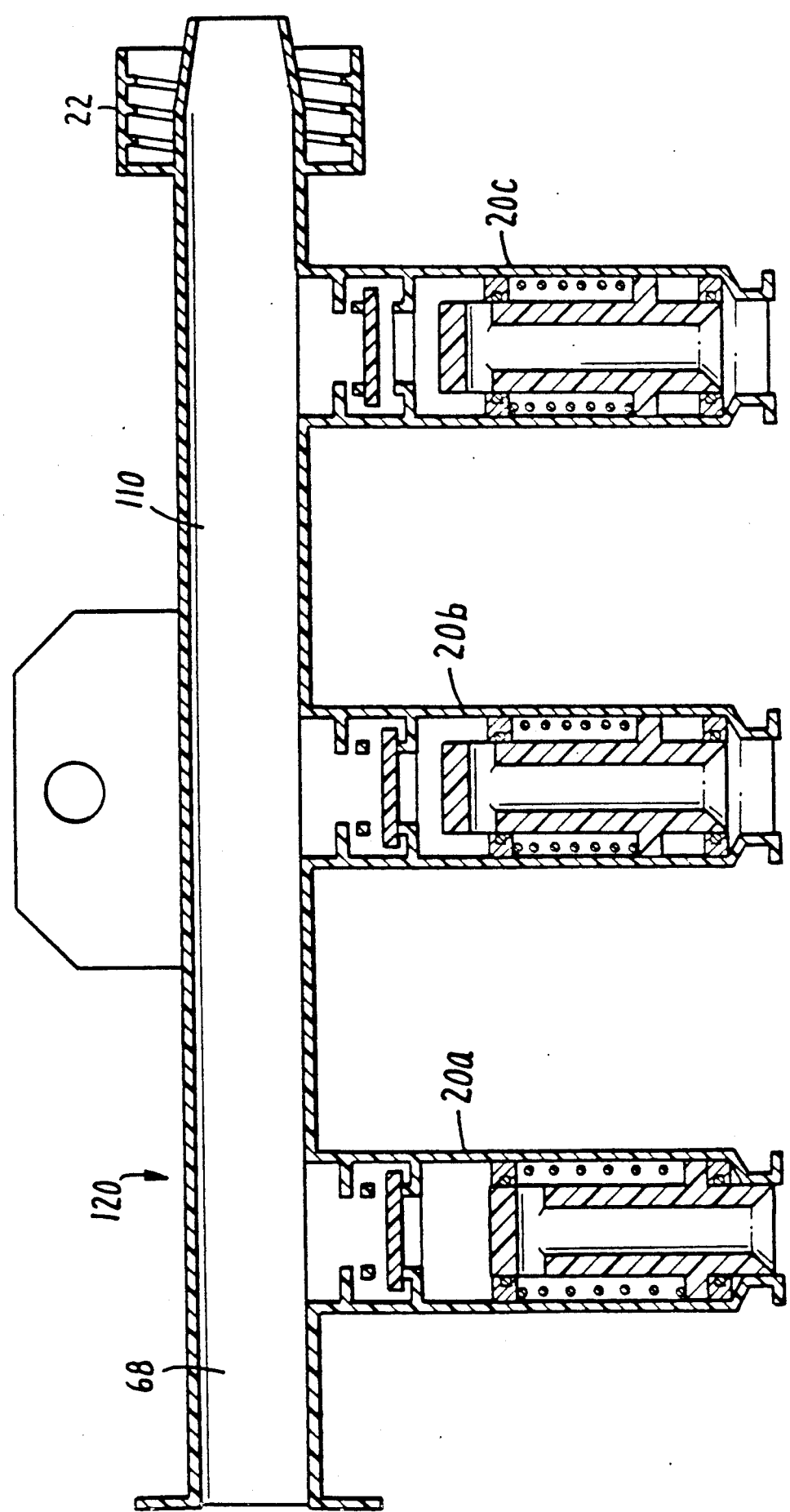
FIG. 4 is a cross-sectional view of the parenteral fluid injector shown in FIG. 3.

Referring to FIG. 4 there is shown a cross-sectional view of the injector 2 . The injector 120 comprises a plurality of injectors 20 all as shown and described in FIG. 2 connected in tandum to a fluid flow line 110. The fluid flow line 110 may be thought of as simply as another part of the IV line 10. The operation of each of the injectors 20 shown in the injector 120 is identical to that shown a described in FIG. 2. The advantages of the injector 120 is that a plurality of syringes 26, or other IV lines 58 (FIG. 1b), or a combination of such, containing different medications or IV fluids (blood, plasma, antibiotic drips) can be connected "on-line" and be available for instantaneous and intermittent delivery thereof to the patient 14. In many surgical procedures, it is often desirable and necessary to administer a plurality of different drugs or different fluids "on demand". Thus, the injector 120 of the present invention provides this capability with all the attending advantages of safety to the patient as previously described. The injector 20a is shown in a "closed" state, i.e., no syringe 26 is connected to the injector 20a. The injector 20b is shown in the "on-line" state, i.e., a syringe 26 is connected to the injector 20b but the anti-backflow member is closed. The injector 20c is shown in the "open" state, i.e., a syringe 26 is connected to the injector 20c and fluid is being injected into the IV flow line 110.

Referring to FIG. 5 there is shown another embodiment of the injector 20 of the present invention. This embodiment comprises an injector 20 made to be attached directly to a needle or IV catheter. The one end 22 of the injector 20 comprises a male "luer" lock connector for connection to a needle or similar device. The other end 24 of the fluid injector 20 comprises a female "luer" lock connector and is adapted to receive the needle-less tip of the syringe 26 which has a male "luer" lock connector for attachment to the female luer lock connector 24. Thus, with the male luer lock 22 and the female luer lock 24, the fluid injector 20 is securely connected to the needle (or similar device) and to the syringe. When this embodiment of the injector 20 of the present invention is directly attached to an IV catheter (as 12 in FIG. 3) inserted into a patient (as 14 in FIG. 3) it may then be used for subsequent needle-less IV injections or needle-less withdrawing of blood samples from the patient 14 with a syringe 26 attached to end connector 24. Besides the immense advantage of being able to perform the aforementioned without the use of subsequent needles, the advantage of patient comfort is also made possible. Intermittent repeated needle-less IV injections or removal of blood samples are possible from a single venipuncture. Patient comfort and health care worker protection are both achieved.

When this embodiment of injector 20 of the present invention is directly attached to a free needle, the resulting needle and injector 20 combination may then be inserted into a standard, present day use, rubber plug port in an IV line. This then essentially converts the standard needle-requiring rubber plug port into a needle-less parenteral fluid injector 20 of the current inven-

What is claimed is:

1. A parenteral fluid and medication injector for use with a fluid transport means having one end for connection to a patient and a fluid input port for receiving a fluid or medication, wherein the improvement comprising:

a fluid conduit having a fluid path connecting two ends; a first end for receiving said fluid or medication, and a second end along said fluid path downstream from said first end having means for connecting to said fluid input port of said fluid transport means for dispensing said fluid or medication into said fluid transport means;

a first valve means, located at said second end of said fluid conduit, for preventing backflow of said fluid or medication from the second end of said fluid conduit to the first end to dilute the fluid or medication at said first end; and a second valve means, located along said fluid path upstream from said first valve means at said first end of said fluid conduit, for preventing air embolus in said fluid conduit, and for receiving said fluid or medication for injection into said fluid transport means.

2. The injector of claim 1 wherein said first valve means is a member movable under fluid pressure alone, between a first position, wherein fluid can flow in said conduit between said two ends, and a second position, wherein fluid cannot flow between said two ends.

3. The injector of claim 1 wherein said second valve means further comprising:

an injection piston in said fluid conduit, movable between a first position and a second position;

said piston having a central bore for the passage of said fluid; said piston having a capped end and an injection inlet port;

spring urging means for urging said piston in said first position;

sealing means between said piston and said fluid conduit for sealing said fluid flow between said inlet port and said fluid transport means, when said piston is in said first position; and means for permitting fluid flow between said inlet port and said fluid transport when said piston is in said second position.

4. The injector of claim 3 wherein said sealing means is an O-ring.

5. The injector of claim 3 wherein said spring urging means is a spring.

6. The injector of claim 1 wherein said fluid transport means has a plurality of input ports.

7. The injector of claim 6 further comprising a plurality of said fluid conduits, each fluid conduit connected to one of said fluid input ports of said fluid transport means, each fluid conduit comprising said first valve means and said second valve means.

8. The injector of claim 7 wherein each of said second valve means further comprising:

an injection piston in said fluid conduit, movable between a first position and a second position;

said piston having a central bore for the passage of said fluid; said piston having a capped end and an injection inlet port;

spring urging means for urging said piston in said first position;

sealing means between said piston and said fluid conduit for sealing said fluid flow between said inlet port and said fluid transport means, when said piston is in said first position; and means for permitting fluid flow between said inlet port and said fluid transport when said piston is in said second position.

9. The injector of claim 8 wherein said sealing means is an O-ring.

10. The injector of claim 8 wherein said spring urging means is a spring.

11. A parenteral fluid and medication injector for use with a fluid transport means having one end for connection to a patient and a fluid input port for receiving a fluid or medication diluted by a diluting fluid, forming a diluted fluid, said injector comprising:

a first port for connecting to said fluid input port and for dispensing said diluted fluid;

a second port for receiving said diluting fluid;

a third port for receiving said fluid or medication;

a first fluid conduit connecting said first, second and third ports;

injection means connected to third port; said injection means comprising a second fluid conduit having a fluid path connecting two ends; a first end for receiving said fluid or medication, and a second end along said fluid path downstream from said first end having means for connecting to said third port for dispensing said fluid or medication;

a first valve means, located at said second end of said second fluid conduit, for preventing backflow of said diluted fluid to the first end to dilute the fluid or medication at said first end; and a second valve means, located along said fluid path upstream from said first valve means at said first end of said second fluid conduit, for preventing air embolus in said second fluid conduit, and for receiving said fluid or medication for injection into said fluid transport means.

* * * * *